United States Patent [19]

Bach et al.

[11] 4,110,339

[45] Aug. 29, 1978

[54] 4-(DI-n-PROPYL)AMINO-1,3,4,5-TETRAHYDROBENZ[cd]INDOLE

[75] Inventors: Nicholas J. Bach; Edmund C. Kornfeld, both of Indianapolis, Ind.

[73] Assignee: Eli Lilly and Company, Indianapolis, Ind.

[21] Appl. No.: 854,878

[22] Filed: Nov. 25, 1977

[51] Int. Cl.$^2$ ............................................. C07D 209/90
[52] U.S. Cl. ........................... 260/326.9; 260/326.5 B; 424/274
[58] Field of Search ....................................... 260/326.9

[56] References Cited

U.S. PATENT DOCUMENTS 3,200,130   8/1965   Szmuszkovicz ................... 260/326.9

OTHER PUBLICATIONS

Harris et al., J. Pharmacol. Exptl. Therap., vol. 128, pp. 358–362 (1960).
Cassady et al., J. Med. Chem., vol. 17, pp. 300–307 (1974).
Stoll et al., Helv. Chim. Acta., vol. 35, pp. 148–152.
Kornfeld et al, J. Am. Chem. Soc., vol. 78, pp. 3087–3114 (1956).

*Primary Examiner*—Alton D. Rollins
*Attorney, Agent, or Firm*—James L. Rowe; Arthur R. Whale

[57] ABSTRACT

4-(Di-n-propyl)amino-1,3,4,5-tetrahydrobenz[cd]-indole, useful as prolactin inhibitor and in treatment of Parkinsonisn.

3 Claims, No Drawings

4-(DI-n-PROPYL)AMINO-1,3,4,5-TETRAHYDROBENZ[cd]INDOLE

BACKGROUND OF THE INVENTION 4-(Dimethyl)amino-1,3,4,5-tetrahydrobenz[cd]indole was prepared by Stoll and Petrzilka, *Helv. Chim. Acta.*, 35, 148 (1952). The compound was used as an intermediate in a Hofmann degradation. 4-Amino-1,3,4,5-tetrahydrobenz[cd]indole is disclosed in *J. Pharm. Exptl. Therap.*, 128, 358 (1960) as a 5-hydroxytryptophane antagonist.

SUMMARY OF THE INVENTION

This invention provides 4-(di-n-propyl)amino-1,3,4,5-benz[cd]indole having the following structure:

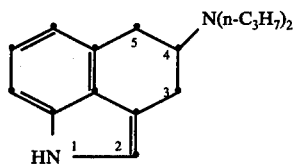

Pharmaceutically-acceptable acid addition salts of the above compound come within the scope of this invention and include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The above compound is prepared according to the following procedure. 1-Benzoyl-4-bromo-5-keto-1,2,2a,3,4,5-hexahydrobenz[cd]indole prepared by the method of Kornfeld et al., *J. Am. Chem. Soc.*, 78, 3087 (1956) (Compound 13 page 3089; preparation page 3098) is reduced with sodium borohydride to yield the bromoalcohol, which compound upon treatment with zinc and acetic acid yields the corresponding $\Delta^4$ derivative. Treatment of this unsaturated compound with m-chloroperbenzoic acid yields the 4,5-epoxide which upon reaction with magnesium bromide or zinc iodide rearranges to give 1-benzoyl-4-keto-1,2,2a,3,4,5-hexahydrobenz[cd]indole. This procedure is set forth in Cassady et al., *J. Med. Chem.*, 17 300 (1974). Alternatively, according to the procedure of Kornfeld et al. (loc. cit.) 1-benzoyl-5-keto-1,2,2a,3,4,5-hexahydrobenz[cd]indole can be reduced with sodium borohydride in ethanol to yield the corresponding 5-hydroxy derivative. This hydroxy group is alpha to a benzene ring and can be brominated with PBr$_3$ in benzene to yield 1-benzoyl-5-bromo-1,2,2a,3,4,5-hexahydrobenz[cd]indole. Treatment of this compound with base as for example 2,6-dimethylpyridine provides the desired $\Delta^4$ derivative which can be epoxidized and rearranged to the 4-keto derivative as above.

The 1-benzoyl-4-keto-1,2,2a,3,4,5-hexahydrobenz[cd]indole is reductively aminated with ammonium acetate and sodium cyanoborohydride to yield the corresponding 4-amino derivative. Reductive alkylation with two moles of propionaldehyde, again using sodium cyanoborohydride as the reducing agent, furnishes 1-benzoyl-4-(di-n-propyl)amino-1,2,2a,3,4,5-hexahydrobenz[cd]indole. Next, the benzoyl group is removed, as by acidic hydrolysis, and MnO$_2$ oxidation forms the $\Delta^2$ double bond to yield 4-(di-n-propyl)amino-1,3,4,5-tetrahydrobenz[cd]indole of this invention.

A specific preparation of the compound of this invention follows.

EXAMPLE 1

A suspension of 5 g. of 1-benzoyl-4-bromo-5-keto-1,2,2a,3,4,5-hexahydrobenz[cd]indole was prepared in 200 ml. of ether. 2 g. of sodium borohydride and 50 ml. of methanol were added and the reaction mixture stirred for 35 minutes. The reaction mixture was then diluted with water and the aqueous layer extracted with ethyl acetate. The ethyl acetate layer was separated, washed with water and with saturated aqueous sodium chloride. The organic layer was dried and the solvent removed by evaporation to dryness. Thin layer chromatography indicated that the resulting residue was a single spot material and consisted of 1-benzoyl-4-bromo-5-hydroxy-1,2,2a,3,4,5-hexahydrobenz[cd]indole. The residue was dissolved in 50 ml. of acetic acid. 10 g. of zinc dust were added and the resulting mixture refluxed for 1¾ hours under a nitrogen atmosphere. Thin layer chromatography of an aliquot indicated that one major spot was present. The reaction mixture was filtered and the filtrate poured over ice. The resulting aqueous mixture was made basic with 14N aqueous ammonium hydroxide. The alkaline layer was then extracted with ethyl acetate. The ethyl acetate extract was separated, washed with water and with saturated aqueous sodium chloride and then dried. Evaporation of the solvent yielded a residue which was shown by thin layer chromatography to consist of one major spot with a small spot corresponding to starting material. A chloroform solution of the residue was filtered through florisil and the residue obtained after the evaporation of chloroform in vacuo was crystallized from methanol to yield crystalline 1-benzoyl-1,2,2a,3-tetrahydrobenz[cd]indole melting at 89°–91° C.

A solution was prepared from 2.71 g. of 1-benzoyl-1,2,2a,3-tetrahydrobenz[cd]indole in 100 ml. of chloroform. A second solution containing 2.1 g. of 85% m-chloroperbenzoic acid in 100 ml. of chloroform was added. The reaction mixture was stirred at ambient temperature for 4¼ hours. TLC of an aliquot of the solution indicated that most of the starting material had been comsumed. The reaction mixture was diluted with water and the organic layer washed with 1N aqueous sodium hydroxide, with water and with saturated aqueous sodium chloride. The organic layer was dried and the solvent removed therefrom by evaporation in vacuo. The resulting residue containing 1-benzoyl-4,5-epoxy-1,2,2a,3,4,5-hexahydrobenz[cd]indole formed in the above reaction was dissolved in chloroform and the chloroform solution filtered through florisil. The chloroform was evaporated from the filtrate and the resulting residue crystallized from a mixture of ether and hexane, yielding 1-benzoyl-4,5-epoxy-1,2,2a,3,4,5-hexahydrobenz[cd]indole melting in the range 103°–115° C. (the above procedure is based upon that of Kornfeld et al., *J. Am. Chem. Soc.*, 78, 3101 (1956))

Twenty grams of 1-benzoyl-4,5-epoxy-1,2,2a,3,4,5-hexahydrobenz[cd]indole were dissolved in 500 ml. of benzene. 7.7 g. of zinc iodide were added and the resulting mixture refluxed under nitrogen for about 1.5 hours. Thin layer chromatrography indicated one major spot slightly slower than the spot corresponding to starting material. The reaction mixture was cooled and then diluted with ethyl acetate. The resulting organic layer was washed with water, and with saturated aqueous sodium chloride and was then dried. Evaporation of the solvent yielded a residue comprising 1-benzoyl-4-keto-1,2,2a,3,4,5-hexahydrobenz[cd]indole formed in the above reaction. The residue was crystallized by trituration with ether containing a small amount of benzene, yielding crystals melting at 146°–149° C. (yield equals 16.9 g.)

Four and six-tenths grams of 1-benzoyl-4-keto-1,2,2a,3,4,5-hexahydrobenz[d]indole and 12.4 g. of ammonium acetate were suspended in 400 ml. of methanol. 1.07 g. of sodium cyanoborohydride were added and the resulting mixture stirred at ambient temperature for 17 hours. The reaction mixture was then poured over a mixture of ice and 1N aqueous hydrochloric acid. This mixture was washed with ether and the resulting organic layer discarded. The aqueous layer was then made basic with 14N ammonium hydroxide and the alkaline layer extracted several times with a mixture of chloroform and isopropanol. The organic extracts were combined and the combined extracts washed with saturated aqueous sodium chloride and then dried. Evaporation of the solvent yielded 3.9 g. of a foam consisting of 1-benzoyl-4-amino-1,2,2a,3,4,5-hexahydrobenz[cd]indole. The compound was dissolved in 150 ml. of methanol and 700 mg. of sodium cyanoborohydride were added followed by 6.6 ml. of propionaldehyde. The resulting reaction mixture was stirred at ambient temperature for 22 hours and then worked up by the same procedure as for the primary amine. A residue was obtained consisting of 5.1 g. of an oil comprising 1-benzoyl-4-(di-n-propyl)amino-1,2,2a,3,4,5-hexahydrobenz[cd]indole. This compound was in turn dissolved in 120 ml. of 6N aqueous hydrochloric acid and the acidic solution refluxed under a nitrogen atmosphere for 45 minutes. The reaction mixture was poured onto ice and the acidic aqueous layer made basic with 14N ammonium hydroxide. The alkaline layer was extracted several times with a chloroform-isopropanol solvent mixture. The organic extracts were combined, the combined extracts washed with saturated aqueous sodium chloride and then dried. Evaporation of the solvent in vacuo yielded 3.6 g. of 4-(di-n-propyl)amino-1,2,2a,3,4,5-hexahydrobenz[cd]indole formed in the above reaction.

The product from the above acid treatment was dissolved in 250 ml. of chloroform to which was added 20 g. of manganese dioxide. The reaction mixture was stirred at ambient temperature for 5 hours. Thin layer chromatography of the reaction mixture indicated one major spot. The reaction mixture was filtered and the filtrate was evaporated to dryness in vacuo. The resulting residue was chromatographed over 150 g. of florisil using chloroform containing increasing amounts of methanol (0 to 4%) as eluant. The chromatogram was followed by TLC and fractions shown to contain 4-(di-n-propyl)amino-1,3,4,5-tetrahydrobenz[cd]indole were combined; weight equal 1.5 g. The compound was dissolved in 50 ml. of anhydrous ethanol. 750 mg. of oxalic acid dihydrate in 15 ml. of anhydrous ethanol were added. The solvent was evaporated and the oxalic acid salt of 4-(di-n-propyl)amino-1,3,4,5-tetrahydrobenz[cd]indole recrystallized from acetone to yield crystals melting at 194°–196° C.

Analysis Calc.: C, 65.88; H, 7.57; N, 8.09. Found: C, 65.74; H, 7.33; N, 7.85.

EXAMPLE 2

Preparation of 1-benzoyl-4-amino-1,2,2a,3,4,5-hexahydrobenz[cd]indole

A reaction mixture was prepared from 2.7 g. of 1-benzoyl-4-keto-1,2,2a,3,4,5-hexahydrobenz[cd]indole, 7.7 g. of ammonium acetate and 125 ml. of ethanol. 590 mg. of sodium cyanoborohydride were added and the resulting suspension stirred at ambient temperature for 22 hours. The reaction mixture was then poured over an ice-1N hydrochloric acid mixture and the acidic aqueous layer extracted with chloroform. The aqueous layer was then made basic with 14N aqueous ammonium hydroxide and the alkaline layer extracted several times with chloroform. The chloroform extracts were combined and the combined extracts washed with saturated aqueous sodium chloride and then dried. Evaporation of the chloroform yielded a residue which was shown to be essentially one spot material by TLC. The residue was recrystallized from a mixture of methylene dichloride and ether to yield crystals of 1-benzoyl-4-amino-1,2,2a,3,4,5-hexahydrobenz-[cd]indole melting at 118°–120° C.; yield 825 mg.

Analysis Calc.: C, 77.67; H, 6.52; N, 10.06. Found: C, 77.91; H, 6.72; N, 10.27.

EXAMPLE 3

Preparation of Salts

Salts of the free bases of this invention are prepared by dissolving the free base in ether and adding an equivalent of a suitable non-toxic acid, for example, maleic acid, also in ether. The salt thus formed, as for example the maleate salt, is insoluble in ether and can be isolated by filtration. Alternatively, the amine base can be dissolved in ethanol and an equivalent of the acid, for example, sulfuric acid, added as an ethanolic solution. In this instance, since the salt thus formed is soluble in the reaction mixture, the salt is isolated by evaporation of the solvent in vacuo. Salts which can be formed by the above procedures include, among others, the hydrochloride, hydrobromide, phosphate, hydrogen phosphate, dihydrogen phosphate, acetate, succinate, tartrate, citrate, benzoate, and p-toluene sulfonate salts.

Specifically, 3.5 millimoles of 4-(di-n-propyl)amino-1,3,4,5-tetrahydrobenz[cd]indole were dissolved in 30 ml. of anhydrous ethanol. The solution was heated to reflux and 2.5 millimoles of oxalic acid dihydrate in 10 ml. of anhydrous ethanol were added. The mixture was cooled and the oxalate salt separated by filtration; melting point = 194°–196° C. with decomposition; weight = 305 mg.

The compounds of this invention are prolactin inhibitors. They manifest this activity in a standard test employing reserpinized rats at a dose level of 50 mcg/kg. As prolactin inhibitors, the compounds are useful in the treatment of disease conditions in which an excess of prolactin is present as in inappropriate lactation. In addition, the compounds affect turning behavior in rats as determined by the procedure of Ungerstedt and Arbuthnott, *Brain Research*, 24, 485 (1970). As such, the compounds are potentially useful in the treatment of Parkinsons syndrome. Finally the compounds of this invention have been shown to be inhibitors of dopamine binding to bovine striatal membrane fragments. The concentration of 4-(di-n-propyl)amino-1,3,4,5-tetrahydrobenz[cd]indole necessary to inhibit 50% of the dopamine binding ($IC_{50}$) was 140 nano moles.

In using 4-(di-n-propyl)amino-1,3,4,5-tetrahydrobenz[cd]indole as a prolactin inhibitor or for other pharmacologic use, the compound or a pharmaceutically-acceptable salt thereof is dissolved or suspended in a suitable liquid pharmaceutical extending medicine and administered by parenteral injection. Alternatively, for oral administration, the compound or a salt thereof is mixed with one or more pharmaceutical excipients and formed into tablets or pills or loaded into empty telescoping gelatin capsules.

We claim:

1. 4-(Di-n-propyl)amino-1,3,4,5-tetrahydrobenz[cd]indole and pharmaceutically-acceptable acid addition salts thereof.

2. A base according to claim 1, said base being 4-(di-n-propyl)amino-1,3,4,5-tetrahydrobenz[cd]indole.

3. The oxalate salt of the base of claim 2.

* * * * *